(12) United States Patent
Jang et al.

(10) Patent No.: US 9,233,061 B2
(45) Date of Patent: Jan. 12, 2016

(54) COSMETIC COMPOSITION COMPRISING HIGH CONCENTRATION CAFFEINE AND NIACINAMIDE

(71) Applicants: Dong Hyuk Jang, Yongin-si (KR); Hwa Young Shin, Yongin-si (KR); Chang Hoon Park, Yongin-si (KR); Sang Hoon Han, Yongin-si (KR)

(72) Inventors: Dong Hyuk Jang, Yongin-si (KR); Hwa Young Shin, Yongin-si (KR); Chang Hoon Park, Yongin-si (KR); Sang Hoon Han, Yongin-si (KR)

(73) Assignee: AMOREPACIFIC CORPORATION (KR)

( * ) Notice: Subject to any disclaimer, the term of this patent is extended or adjusted under 35 U.S.C. 154(b) by 0 days.

(21) Appl. No.: 14/358,752

(22) PCT Filed: Nov. 16, 2012

(86) PCT No.: PCT/KR2012/009738
§ 371 (c)(1),
(2) Date: May 16, 2014

(87) PCT Pub. No.: WO2013/073894
PCT Pub. Date: May 23, 2013

(65) Prior Publication Data
US 2015/0005326 A1    Jan. 1, 2015

(30) Foreign Application Priority Data

Nov. 16, 2011 (KR) .......................... 10-2011-0119391
Nov. 15, 2012 (KR) .......................... 10-2012-0129688

(51) Int. Cl.
*A61K 8/49* (2006.01)
*A61Q 19/00* (2006.01)
*A61Q 19/06* (2006.01)

(52) U.S. Cl.
CPC .............. *A61K 8/4953* (2013.01); *A61K 8/4926* (2013.01); *A61Q 19/00* (2013.01); *A61Q 19/06* (2013.01); *A61K 2800/52* (2013.01)

(58) Field of Classification Search
USPC ...................................... 544/265; 514/263.32
See application file for complete search history.

(56) References Cited

U.S. PATENT DOCUMENTS

| 5,900,416 A | * | 5/1999 | Markson ....................... 424/728 |
| 5,962,482 A | | 10/1999 | Bissett |
| 2004/0146539 A1 | | 7/2004 | Gupta |

FOREIGN PATENT DOCUMENTS

| CN | 101217999 | | 7/2008 |
| JP | 10182347 | A | 7/1998 |
| KR | 1020030048255 | A | 6/2003 |
| KR | 1020050067837 | A | 7/2005 |
| KR | 1008606050000 | B1 | 9/2008 |
| KR | 1020110085544 | A | 7/2011 |
| WO | 9727750 | | 8/1997 |
| WO | 2007007255 | | 1/2007 |

OTHER PUBLICATIONS

International Search Report with English Translation for International Application No. PCT/KR2012/009738 dated Mar. 25, 2013.
Written Opinion for International Application No. PCT/KR2012/009738 dated Mar. 25, 2013.
CN Office Action-CN Application No. 201280067250.6 dated Jul. 14, 2015, citing the enumerated refereneces listed above.

* cited by examiner

*Primary Examiner* — Kristin Vajda
(74) *Attorney, Agent, or Firm* — Cantor Colburn LLP

(57) ABSTRACT

A cosmetic composition according to the present invention may prevent the precipitation of caffeine at a low temperature, and thus may comprise a high concentration of caffeine that is effective in promoting lipolysis. Caffeine is known to promote lipolysis when applied to a human body. The cosmetic composition of the present invention may comprise a high concentration of caffeine, and thus can be valuably use in cosmetics or the like that requires effects of caffeine such as slimming effects, effect of relief from facial swelling or the like.

6 Claims, No Drawings

COSMETIC COMPOSITION COMPRISING HIGH CONCENTRATION CAFFEINE AND NIACINAMIDE

TECHNICAL FIELD

The present disclosure relates to a cosmetic composition containing high-concentration caffeine and niacinamide.

BACKGROUND ART

Fat is accumulated in the human body in adipocytes, the main sites of fat storage in the body, in the form of triacylglycerol. The lipolytic enzyme triacylglycerol lipase is activated by cyclic adenosine monophosphate (cAMP) and degrades fats into triglycerides and fatty acids.

Caffeine can increase the amount of cAMP by inhibiting the activity of nucleotide phosphodiesterase and, thus, can promote lipolysis by enhancing the activity of triacylglycerol lipase. However, because the solubility of caffeine in water at room temperature is only about 2%, its content in cosmetics is restricted. Even if caffeine could be dissolved, it may be precipitated if the temperature is lowered. Accordingly, its use in cosmetics is limited.

Niacinamide has been used to achieve skin-whitening effect in the field of cosmetics as disclosed in Korean Patent Registration No. 10-0860605 or Korean Patent Publication No. 10-2011-0085544.

The inventors of the present disclosure have made efforts to solve the above-described problem. As a result, they have found out that when caffeine is used together with niacinamide, niacinamide prevents precipitation of caffeine and improves the stability of a solution in which caffeine is dissolved at low temperatures.

DISCLOSURE

Technical Problem

The present disclosure is directed to providing a cosmetic composition containing high-concentration caffeine.

Technical Solution

In a general aspect, the present disclosure provides a cosmetic composition containing caffeine and niacinamide.

Advantageous Effects

A cosmetic composition according to the present disclosure may prevent precipitation of caffeine at low temperatures and, thus, may contain caffeine, which is effective in promoting lipolysis, at high concentrations. Caffeine is known to promote lipolysis when applied to the human body. Since the cosmetic composition according to the present disclosure can contain caffeine at high concentrations, it can be useful in cosmetics, etc. requiring the effects of caffeine such as slimming effect, facial swelling-relieving effect, etc.

BEST MODE

In an aspect, the present disclosure relates to a cosmetic composition containing caffeine and niacinamide.

Caffeine ($C_8H_{10}O_2N_4$) is a bitter-tasting, white crystalline xanthine alkaloid having three methyl groups, which is sparingly soluble in cold water but very soluble in hot water. Caffeine has pharmacological activities as a central nervous system stimulant, cardiac stimulant, diuretic, etc. and is effective in degrading fats, especially cellulite. Specifically, caffeine can increase the amount of cAMP by inhibiting the activity of nucleotide phosphodiesterase and, thus, can promote lipolysis by enhancing the activity of triacylglycerol lipase.

Niacinamide ($C_6H_6N_2O$), also known as nicotinamide, has been used in the field of cosmetics mainly to achieve skin-whitening effect. Since niacinamide has hydrotropic property, it may be used as a cosolubilizing agent for helping dissolution of sparingly soluble substances. The term hydrotropy refers to the ability of a compound which increases the solubility of water-insoluble or sparingly soluble compounds in water. The term solubilizing agent refers to a substance which forms a stable emulsion of two mutually immiscible liquids and is also called an emulsifying agent.

Since the cosmetic composition according to the present disclosure can prevent precipitation of caffeine at low temperatures, it can contain caffeine which is effective in promoting lipolysis at high concentrations. Caffeine is known to promote lipolysis when applied to the human body. Since the cosmetic composition according to the present disclosure can contain caffeine at high concentrations, it can be useful in cosmetics, etc. requiring the effects of caffeine such as slimming effect, facial swelling-relieving effect, etc.

In an exemplary embodiment of the present disclosure, the cosmetic composition may contain 1-10 wt % of caffeine based on the total weight of the composition. In this case, a weight ratio of niacinamide to caffeine may be from 0.5 to 2. If the content of caffeine is less than 1 wt %, the desired effect of promoting lipolysis may be insufficient although the composition does not need the special measure for stabilization because of relatively easy dissolution. And, if the content exceeds 10 wt %, an excessive amount of niacinamide is necessary for solubilization and, even if the caffeine is dissolved, rapid precipitation may be induced during long-term storage due to nucleation occurring on the container wall as a result of local water evaporation. If the weight ratio of niacinamide to caffeine is smaller than 0.5, caffeine may precipitation at room temperature and low temperatures. And, a weight ratio greater than 2 is excessively high considering that the recommended standard for skin-whitening cosmetics is 2-5%. In another exemplary embodiment of the present disclosure, the cosmetic composition may contain 1-3 wt % of caffeine based on the total weight of the composition and, in this case, the weight ratio of niacinamide to caffeine may be from 0.5 to 1. In another exemplary embodiment of the present disclosure, the cosmetic composition may contain 3-5 wt % of caffeine based on the total weight of the composition and, in this case, the weight ratio of niacinamide to caffeine may be from 1 to 1.5. In another exemplary embodiment of the present disclosure, the cosmetic composition may contain 5-10 wt % of caffeine based on the total weight of the composition and, in this case, the weight ratio of niacinamide to caffeine may be from 1 to 2.

TABLE 1

| Caffeine content | Niacinamide/caffeine weight ratio |
|---|---|
| 1-3% | 0.5-1 |
| 3-5% | 1-1.5 |
| 5-10% | 1-2 |

The contents of niacinamide presented in Table 1 are recommended minimal values for ensuring stability against precipitation of caffeine at low temperatures and higher contents may be used if necessary. The presented niacinamide contents are based on an aqueous solution and may be decreased or increased slightly depending on the ingredients added to prepare various cosmetic formulations, such as ethanol, polyol, polymers, surfactants, oil, extracts, pH adjusting agents, etc. In addition, the presented niacinamide contents will vary depending on the age, sex and body weight of a subject and the discretion of a diagnoser. Determination of the administration dose considering these factors is within the level of those skilled in the art.

The cosmetic composition according to the present disclosure may be prepared into softening lotion, astringent lotion, nourishing lotion, nourishing cream, massage cream, eye cream, eye essence, essence, cleansing cream, cleansing lotion, cleansing foam, cleansing water, pack, makeup base, foundation, body lotion, body cream, body essence, body cleanser, emulsion, lotion, ointment, gel, cream, patch or spray.

The cosmetic composition according to the present disclosure may be used as a cosmetic composition for promoting lipolysis, a cosmetic composition for slimming or an anti-cellulite cosmetic composition. The cosmetic composition may be directly applied on the parts abundant in subcutaneous fat, such as face, abdomen, thighs, buttocks, arms, etc., to reduce fats in those parts and may be prepared to be suitable for application to the skin, although not particularly limited in formulation.

MODE FOR INVENTION

Hereinafter, the present disclosure will be described in detail through examples. However, the following examples are for illustrative purposes only and it will be apparent to those of ordinary skill in the art that the scope of the present disclosure is not limited by the examples.

Example 1

Caffeine Solubility at Room Temperature

While adding caffeine powder to 100 g of 0-10 wt % niacinamide solution with agitation mixing at 200 rpm, the time when recrystallization started was observed.

TABLE 2

| Niacinamide content | Caffeine solubility (room temperature) |
|---|---|
| 0% | 2.1% |
| 0.5% | 3.1% |
| 1% | 3.6% |
| 2% | 4.6% |
| 3% | 5.7% |
| 5% | 7.9% |
| 10% | 13.6% |

Example 2

Precipitation of Caffeine at Low Temperature (4° C.)

Caffeine is soluble in water up to about 2% at room temperature. However, at low temperature, there is a risk of precipitation if caffeine concentration is 1% or greater because of decreased solubility. In order to investigate the effect of inhibiting caffeine precipitation by niacinamide at low temperature, caffeine and niacinamide were dissolved at room temperature and it was observed whether precipitation occurred after storing for 3 days in a refrigerator.

TABLE 3

| Caffeine content | Amount of niacinamide necessary for inhibiting precipitation |
|---|---|
| 1-3% | 0.5-1 time based on caffeine |
| 3-5% | 1-1.5 times based on caffeine |
| 5-10% | 1-2 times based on caffeine |

Hereinafter, the present disclosure will be described in detail through formulation examples. However, the following formulation examples are for illustrative purposes only and the scope of the present disclosure is not limited by thereby.

Formulation Example 1

Nourishing Lotion (Milk Lotion)

The cosmetic composition according to the present disclosure was prepared into nourishing lotion (milk lotion) with the composition described in Table 4.

TABLE 4

| Ingredients | wt % | | |
|---|---|---|---|
| Caffeine | 2.0 | 4.0 | 7.0 |
| Niacinamide | 1.5 | 5.0 | 8.5 |
| Squalane | 5.0 | 5.0 | 5.0 |
| Beeswax | 4.0 | 4.0 | 4.0 |
| Polysorbate 60 | 1.5 | 1.5 | 1.5 |
| Sorbitan sesquioleate | 1.5 | 1.5 | 1.5 |
| Liquid paraffin | 0.5 | 0.5 | 0.5 |
| Caprylic/capric triglyceride | 5.0 | 5.0 | 5.0 |
| Glycerin | 3.0 | 3.0 | 3.0 |
| Butylene glycol | 3.0 | 3.0 | 3.0 |
| Propylene glycol | 3.0 | 3.0 | 3.0 |
| Carboxyvinyl polymer | 0.1 | 0.1 | 0.1 |
| Triethanolamine | 0.2 | 0.2 | 0.2 |
| Preservative, pigment and fragrance | adequate | adequate | adequate |
| Purified water | to 100 | to 100 | to 100 |

Formulation Example 2

Softening Lotion (Skin Lotion)

The cosmetic composition according to the present disclosure was prepared into softening lotion (skin lotion) with the composition described in Table 5.

TABLE 5

| Ingredients | wt % | | |
|---|---|---|---|
| Caffeine | 2.0 | 4.0 | 7.0 |
| Niacinamide | 1.5 | 5.0 | 8.5 |
| Glycerin | 3.0 | 3.0 | 3.0 |
| Butylene glycol | 2.0 | 2.0 | 2.0 |
| Propylene glycol | 2.0 | 2.0 | 2.0 |
| Carboxyvinyl polymer | 0.1 | 0.1 | 0.1 |
| PEG 12 nonyl phenyl ether | 0.2 | 0.2 | 0.2 |
| Polysorbate 80 | 0.4 | 0.4 | 0.4 |
| Ethanol | 10.0 | 10.0 | 10.0 |
| Triethanolamine | 0.1 | 0.1 | 0.1 |
| Preservative, pigment and fragrance | adequate | adequate | adequate |
| Purified water | to 100 | to 100 | to 100 |

Formulation Example 3

Nourishing Cream

The cosmetic composition according to the present disclosure was prepared into nourishing cream with the composition described in Table 6.

TABLE 6

| Ingredients | wt % | | |
|---|---|---|---|
| Caffeine | 2.0 | 4.0 | 7.0 |
| Niacinamide | 1.5 | 5.0 | 8.5 |
| Polysorbate 60 | 1.5 | 1.5 | 1.5 |
| Sorbitan sesquioleate | 0.5 | 0.5 | 0.5 |
| PEG60 hydrogenated castor oil | 2.0 | 2.0 | 2.0 |
| Liquid paraffin | 10 | 10 | 10 |
| Squalane | 5.0 | 5.0 | 5.0 |
| Caprylic/capric triglyceride | 5.0 | 5.0 | 5.0 |
| Glycerin | 5.0 | 5.0 | 5.0 |
| Butylene glycol | 3.0 | 3.0 | 3.0 |
| Propylene glycol | 3.0 | 3.0 | 3.0 |
| Triethanolamine | 0.2 | 0.2 | 0.2 |
| Preservative | adequate | adequate | adequate |
| Pigment | adequate | adequate | adequate |
| Fragrance | adequate | adequate | adequate |
| Purified water | to 100 | to 100 | to 100 |

Formulation Example 4

Massage Cream

The cosmetic composition according to the present disclosure was prepared into massage cream with the composition described in Table 7.

TABLE 7

| Ingredients | wt % | | |
|---|---|---|---|
| Caffeine | 2.0 | 4.0 | 7.0 |
| Niacinamide | 1.5 | 5.0 | 8.5 |
| Beeswax | 10.0 | 10.0 | 10.0 |
| Polysorbate 60 | 1.5 | 1.5 | 1.5 |
| PEG 60 hydrogenated castor oil | 2.0 | 2.0 | 2.0 |
| Sorbitan sesquioleate | 0.8 | 0.8 | 0.8 |
| Liquid paraffin | 40.0 | 40.0 | 40.0 |
| Squalane | 5.0 | 5.0 | 5.0 |
| Caprylic/capric triglyceride | 4.0 | 4.0 | 4.0 |
| Glycerin | 5.0 | 5.0 | 5.0 |
| Butylene glycol | 3.0 | 3.0 | 3.0 |
| Propylene glycol | 3.0 | 3.0 | 3.0 |
| Triethanolamine | 0.2 | 0.2 | 0.2 |
| Preservative, pigment and fragrance | adequate | adequate | adequate |
| Purified water | to 100 | to 100 | to 100 |

Formulation Example 5

Pack

The cosmetic composition according to the present disclosure was prepared into pack with the composition described in Table 8.

TABLE 8

| Ingredients | wt % | | |
|---|---|---|---|
| Caffeine | 2.0 | 4.0 | 7.0 |
| Niacinamide | 1.5 | 5.0 | 8.5 |
| Polyvinyl alcohol | 13.0 | 13.0 | 13.0 |

TABLE 8-continued

| Ingredients | wt % | | |
|---|---|---|---|
| Sodium carboxymethyl cellulose | 0.2 | 0.2 | 0.2 |
| Glycerin | 5.0 | 5.0 | 5.0 |
| Allantoin | 0.1 | 0.1 | 0.1 |
| Ethanol | 6.0 | 6.0 | 6.0 |
| PEG 12 nonyl phenyl ether | 0.3 | 0.3 | 0.3 |
| Polysorbate 60 | 0.3 | 0.3 | 0.3 |
| Preservative, pigment and fragrance | adequate | adequate | adequate |
| Purified water | to 100 | to 100 | to 100 |

Formulation Example 6

Gel

The cosmetic composition according to the present disclosure was prepared into gel with the composition described in Table 9.

TABLE 9

| Ingredients | wt % | | |
|---|---|---|---|
| Caffeine | 2.0 | 4.0 | 7.0 |
| Niacinamide | 1.5 | 5.0 | 8.5 |
| Sodium ethylenediaminetetraacetate | 0.05 | 0.05 | 0.05 |
| Glycerin | 5.0 | 5.0 | 5.0 |
| Carboxyvinyl polymer | 0.3 | 0.3 | 0.3 |
| ethanol | 5.0 | 5.0 | 5.0 |
| PEG 60 hydrogenated castor oil | 0.5 | 0.5 | 0.5 |
| Triethanolamine | 0.3 | 0.3 | 0.3 |
| Preservative, pigment and fragrance | adequate | adequate | adequate |
| Purified water | to 100 | to 100 | to 100 |

While the exemplary embodiments have been shown and described, it will be understood by those skilled in the art that various changes in form and details may be made thereto without departing from the spirit and scope of this disclosure as defined by the appended claims. In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

INDUSTRIAL APPLICABILITY

A cosmetic composition according to the present disclosure may prevent precipitation of caffeine at low temperatures and, thus, may contain caffeine, which is effective in promoting lipolysis, at high concentrations. Caffeine is known to promote lipolysis when applied to the human body. Since the cosmetic composition according to the present disclosure can contain caffeine at high concentrations, it can be useful in cosmetics, etc. requiring the effects of caffeine such as slimming effect, facial swelling-relieving effect, etc.

The invention claimed is:

1. A cosmetic composition comprising caffeine and niacinamide,
    wherein a weight ratio of niacinamide to caffeine is from 1 to 1.5 when the cosmetic composition comprises 3-5 wt % of caffeine based on the total weight of the composition,
    wherein the weight ratio of niacinamide to caffeine is greater than 1 but less than or equal to 2 when the cosmetic composition comprises 5-10 wt % of caffeine based on the total weight of the composition, wherein caffeine precipitation of the cosmetic composition is inhibited at 4° C.

2. The cosmetic composition according to claim 1, wherein the cosmetic composition is for promoting lipolysis.

3. The cosmetic composition according to claim 1, wherein the cosmetic composition is for slimming.

4. A method for improving the stability of caffeine in a cosmetic composition, comprising adding niacinamide to caffeine or the cosmetic composition comprising caffeine, wherein a weight ratio of niacinamide to caffeine is from 1 to 1.5 when the cosmetic composition comprises 3-5 wt % of caffeine based on the total weight of the composition, wherein the weight ratio of niacinamide is greater than 1 but less than or equal to 2 when the cosmetic composition comprises 5-10 wt % of caffeine based on the total weight of the composition, wherein caffeine precipitation of the cosmetic composition is inhibited at 4° C.

5. The method according to claim 4, wherein the cosmetic composition is for promoting lipolysis.

6. The method according to claim 4, wherein the cosmetic composition is for slimming.

* * * * *